(12) United States Patent
Yabe et al.

(10) Patent No.: US 8,454,500 B2
(45) Date of Patent: Jun. 4, 2013

(54) LIGHT SOURCE DEVICE AND ENDOSCOPE SYSTEM

(75) Inventors: Yusuke Yabe, Hachioji (JP); Tomoya Takahashi, Hachioji (JP); Atsushi Shimada, Hachioji (JP); Susumu Hashimoto, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1692 days.

(21) Appl. No.: 11/593,755

(22) Filed: Nov. 7, 2006

(65) Prior Publication Data
US 2007/0149857 A1    Jun. 28, 2007

(30) Foreign Application Priority Data

Dec. 28, 2005 (JP) .................. 2005-379802

(51) Int. Cl.
  *A61B 1/06* (2006.01)
(52) U.S. Cl.
  USPC .......................................................... 600/180
(58) Field of Classification Search
  USPC ...... 600/132, 160, 178, 180, 181; 348/68–69, 348/72
  See application file for complete search history.

(56) References Cited

U.S. PATENT DOCUMENTS

| | | | |
|---|---|---|---|
| 5,868,666 A * | 2/1999 | Okada et al. .................. | 600/118 |
| 5,966,168 A * | 10/1999 | Miyazaki ........................ | 348/68 |
| 5,984,862 A | 11/1999 | Honda et al. | |
| RE36,582 E | 2/2000 | Furuya et al. | |
| 6,511,422 B1 * | 1/2003 | Chatenever .................... | 600/180 |
| 7,226,412 B2 * | 6/2007 | Ueno et al. ..................... | 600/178 |
| 7,258,663 B2 * | 8/2007 | Doguchi et al. ............. | 600/109 |
| 2005/0033116 A1 | 2/2005 | Miyake et al. | |

FOREIGN PATENT DOCUMENTS

| | | |
|---|---|---|
| DE | 41 43 463 C2 | 3/1992 |
| DE | 197 09 424 A1 | 10/1997 |
| EP | 1 721 568 A1 | 11/2006 |
| JP | 11-164811 | 6/1999 |
| JP | 2000-075220 | 3/2000 |
| JP | 2005-279253 | 10/2005 |
| JP | 2005-334007 | 12/2005 |
| WO | WO 2005/112737 A1 | 12/2005 |

* cited by examiner

*Primary Examiner* — Philip R Smith
(74) *Attorney, Agent, or Firm* — Scully, Scott, Murphy & Presser, P.C.

(57) ABSTRACT

An endoscope system of the present invention has a video processor and a light source device, and an endoscope can be connected thereto. And a control portion of the light source device detects connection with the endoscope and the video processor, detects connection with the video processor and the light source device and detects the type of the endoscope by an endoscope detection portion. And when non-connection of the endoscope and the video processor is detected, or non-connection of the video processor and the light source device is detected, the control portion controls so that the light amount of illumination light supplied from the light source device to the endoscope becomes a predetermined light amount according the detected type of the endoscope.

8 Claims, 7 Drawing Sheets

| DIAPHRAGM CONTROL PORTION INPUT SIGNAL | | | DIAPHRAGM CONTROL PORTION OUTPUT SIGNAL | |
|---|---|---|---|---|
| CV_CONNECT | CV_SC | A_M | DRV_DATA | AUTO_MANU |
| L (NOT CONNECTED) | | H (AUTOMATIC) | DIAPHRAGM HALF OPEN VALUE | L (MANUAL) |
| L (NOT CONNECTED) | | L (MANUAL) | D_DATA | L (MANUAL) |
| H (CONNECTED) | L (NOT CONNECTED) | H (AUTOMATIC) | DIAPHRAGM HALF OPEN VALUE | L (MANUAL) |
| H (CONNECTED) | L (NOT CONNECTED) | L (MANUAL) | D_DATA | L (MANUAL) |
| H (CONNECTED) | H (CONNECTED) | H (AUTOMATIC) | D_DATA | H (AUTOMATIC) |
| H (CONNECTED) | H (CONNECTED) | L (MANUAL) | D_DATA | L (MANUAL) |

LIGHT SOURCE DEVICE AND ENDOSCOPE SYSTEM

This application claims benefit of Japanese Application No. 2005-379802 filed in Japan on Dec. 28, 2005, the contents of which are incorporated by this reference.

BACKGROUND OF THE INVENTION

1. Field of the Invention

The present invention relates to a light source device to which an endoscope and an image processing device can be connected and an endoscope system having an image processing device and a light source device and to which an endoscope can be connected.

2. Description of the Related Art

Endoscope devices have been recently used in the medical field and the industrial field. In the medical field, the endoscope is used for observation of organs in a body cavity, for example, and therapeutic treatments using a treatment instrument as necessary. Also, in the industrial field, the endoscope is used for observation and inspection of internal scratches, corrosions and the like in a boiler, a turbine, an engine, a chemical plant and the like.

Some of these endoscope devices are provided with automatic light control means for automatically controlling the brightness of a subject image to be observed. The automatic light control means includes various types, but a type controlling an illumination light amount according to the brightness of the subject image to be observed is one example. Also, when the endoscope device is an electronic endoscope for capturing a subject image by an image pickup device, a device shutter method for controlling the brightness by controlling an accumulation time of charge coupled device as an image pickup device may be employed.

The device shutter method controls the brightness of an image by driving of the image pickup device and is capable of capturing an image with a desired brightness without controlling the light amount of the illumination light. Therefore, in the device shutter method, regardless of the light amount of the illumination light, the illumination light enters the endoscope as it is. This also applies to a case where the light amount of the illumination light is set at the maximum, for example.

Then, Japanese Unexamined Patent Application Publication No. 2000-75220, for example, describes an endoscope light source device which can limit the maximum light amount of illumination light incident to an endoscope when a video signal processing device having the device-shutter type automatic light control means is connected.

However, the endoscope light source device described in the above Japanese Unexamined Patent Application Publication No. 2000-75220 can not receive information on brightness of an image from the video signal processing device in case of defective connection occurring with the video signal processing device and thus, the light amount of the illumination light can not be controlled appropriately. As a result, there is a possibility that an excessively small (minimum, for example) light amount of the illumination light enters the endoscope or an excessively large (maximum, for example) light amount of the illumination light enters the endoscope.

SUMMARY OF THE INVENTION

An object of the present invention is to provide a light source device and an endoscope system which can prevent supply of an excessively small or an excessively large illumination light to an endoscope even if an image processing device and the light source device are not connected.

Briefly, the present invention is a light source device to which an endoscope and an image processing device can be connected and includes a light source of illumination light, connection detecting means for detecting whether the image processing device is connected or not, endoscope detecting means for detecting a type of the connected endoscope, and illumination light control means for controlling so that the light amount of the illumination light becomes a predetermined light amount according to the type of the endoscope detected by the endoscope detecting means when it is detected by the connection detecting means that the image processing device is not connected.

Also, the present invention is an endoscope system including the image processing device and the light source device and to which the endoscope can be connected and further comprises first connection detecting means for detecting whether the endoscope and the image processing device are connected or not, second connection detecting means for detecting whether the image processing device and the light source device are connected or not, endoscope detecting means for detecting the type of the endoscope connected to the light source device, and illumination light control means for control so that a light amount of illumination light supplied from the light source device to the endoscope becomes a predetermined light amount according to the type of the endoscope detected by the endoscope detecting means when it is detected by the first connection detecting means that the endoscope and the image processing device are not connected or it is detected by the second connection detecting means that the image processing device and the light source device are not connected.

The above and other objects, features and advantages of the invention will become more clearly understood from the following description referring to the accompanying drawings.

DETAILED DESCRIPTION OF PREFERRED EMBODIMENT(S)

An embodiment of the present invention will be described below referring to the attached drawings.

FIGS. 1 to 7 show an embodiment of the present invention. The present embodiment is an embodiment of an endoscope system comprising a light source device.

First, an outline of the light source device of the present embodiment will be described.

The light source device of the present embodiment can be set to a manual light control mode and an automatic light control mode. The manual light control mode is a mode to manually control an illumination light amount by an operator using operating means. On the other hand, the automatic light control mode is a mode that the light source device automatically controls the light mount of illumination light on the basis of information relating to brightness of an image extracted by an image processing device from a captured image signal.

The light source device of the present embodiment is configured to be able to control a light amount of the illumination light to a predetermined light amount in the automatic light control mode when connection between the image processing device and the light source device is disconnected for some reason. Cases of disconnection between the light source device and the image processing device include a case where the connection between the image processing device and the light source device is not complete, a case where power of the image processing device is turned off, a case where the endoscope and the image processing device are not connected for naked-eye observation and the like. And by controlling the illumination light amount to the predetermined light amount, a minimum light amount required for observation can be ensured and halation of an image or heat generation due to excessive illumination light can be prevented.

Figure 1:
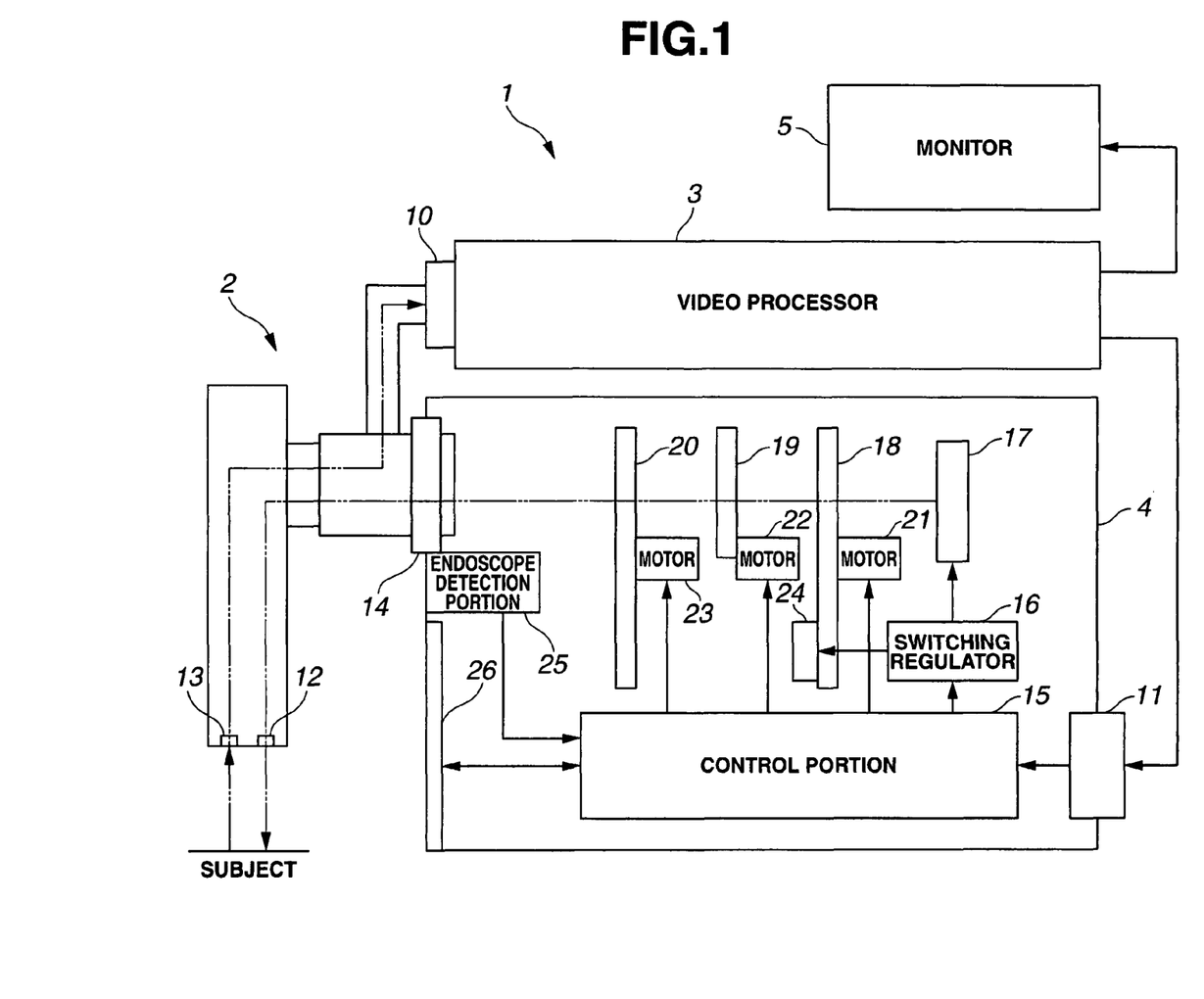
FIG. 1 is a block diagram showing an outline of the configuration of an endoscope system in an embodiment of the present invention.

First, a basic configuration of the endoscope system of the present embodiment will be described. FIG. 1 is a block diagram showing an outline of the configuration of the endoscope system.

As shown in FIG. 1, the endoscope system 1 comprises an endoscope 2, a video processor 3, which is an image processing device provided with a connector 10, a light source device 4 provided with a connector 11 and a connector 14, and a monitor 5.

And the endoscope 2 is connected to the video processor 3 through the connector 10 as well as to the light source device 4 through the connector 14. The video processor 3 is connected to the light source device 4 through the connector 11 and also to the monitor 5.

FIG. 1 shows a state where one endoscope 2 is connected to the endoscope system 1, but there are a plurality of type of endoscopes 2 with different maximum incident light amount which can be connected to the endoscope system 1, and any of them can be selectively connected.

The endoscope 2 is provided with an elongated insertion portion and has a light guide fiber, not shown, internally inserted in the insertion portion. And the endoscope 2 has a lens 12 and a charge coupled device (hereinafter abbreviated as CCD) 13 as an image pickup device at the tip end of the insertion portion.

The video processor 3 has various image processing circuits, not shown, for processing image pickup signals obtained from the CCD 13.

The light source device 4 has a control portion 15 as connection detecting means, first connection detecting means, second connection detecting means, endoscope detecting means, and illumination light control means, a switching regulator 16, a main lamp 17, a turret 18, a diaphragm 19, a light extinction turret 20, a motor 21, a motor 22, a motor 23, a spare lamp 24, an endoscope detection portion 25, and a front panel 26.

When the endoscope 2 is connected to the light source device 4 through the connector 14, the endoscope detection portion 25 outputs an endoscope detection signal to the control portion 15. In the present embodiment, the endoscope detection portion 25 detects the shape of a connection portion of the endoscope 2 with a plurality of photo sensors, not shown, and outputs the endoscope detection signal according to the shape of the connection portion of the endoscope 2. The means to detect the connection of the endoscope 2 is not limited to this but it may be so configured that a microchip or the like storing ID information and the like is provided to the endoscope 2 and such means for detecting the connection of the endoscope 2 is provided that the ID information is read out by the light source device 4.

Also, the front panel 26 provided at the light source device 4 is for an operator to operate the light source device 4. The front panel 26 comprises various display devices for displaying a state and the like of the light source device 4 and various switches, not shown, as operating means arranged on a panel face, and an operation signal corresponding to operation input of the operator is outputted to the control portion 15.

The various switches arranged on this front panel 26 include a light control mode switch, a brightness setting switch and a light-amount setting switch. The light control mode switch is to switch the light source device 4 between the automatic light control mode and the manual light control mode. The brightness setting switch is to set target brightness in the automatic light control mode. When the light source device 4 is switched to the automatic light control mode, light amount control is automatically executed so that an observation image has the set brightness all the time. Moreover, the light-amount setting switch is to set a target light amount. When the light source device 4 is switched to the manual light control mode, control is carried out so that the illumination light of the light amount set by this light-amount setting switch is generated all the time.

The control portion 15 outputs various control signals for controlling the light amount to each portion in the light source device 4 on the basis of the operation signal inputted from the front panel 26. The control signal outputted from the control portion 15 will be described in detail later. The control portion 15 is connected to the connector 11, the switching regulator 16, the motor 21, the motor 22, the motor 23, the endoscope detection portion 25 and the front panel 26 so that signals are received from them or control signals are sent to them.

The switching regulator 16 is a power stabilizer of the type that an inputted voltage is converted to a pulse through high-speed turning on/off (switching) and this pulse is smoothed so as to obtain a stable direct-current voltage. This switching regulator 16 is connected to the main lamp 17, which is a light source, and the spare lamp 24 so as to supply power to them. And the switching regulator 16 also functions as power supply control means which can control power to be supplied.

The main lamp 17 is a bright lamp used for normal observation and configured using a xenon lamp and the like specifically. This main lamp 17 is arranged so that the illumination light passes through the turret 18, the diaphragm 19 and light extinction turret 20.

The spare lamp 24 is a spare light source to be used when defect occurs at the main lamp 17. The spare lamp 24 is a dark lamp as compared with the above-mentioned main lamp 17, and the minimum light amount enabling observation is emitted. This spare lamp 24 is configured using a halogen lamp or the like specifically and arranged on the turret 18.

The turret 18 is a member in the disk shape configured with a plurality of filters such as a normal-light filter, a filter for fluorescent observation and the like and the above-mentioned spare lamp 24 on the coaxial circumferences. And at the center of the disk face of this turret 18, the motor 21 is connected. The motor 21 is to rotate the turret 18 on the basis of the control signal inputted from the control portion 15 so that any one of the filters is located on the light path of the illumination light emitted from the main lamp 17 or so that the spare lamp 24 is located on the light path of the illumination light in the case of defect of the main lamp 17.

Also, the diaphragm 19 is opened/closed to control the light amount incident to the light guide of the endoscope 2 by changing the size of an opening so as to change the passed light amount of the illumination light having passed the turret 18. An opening degree value representing the extent of opening/closing of this diaphragm 19 is controlled by the motor 22 connected to the diaphragm 19. Moreover, this motor 22 is operated on the basis of the control signal inputted from the control portion 15.

The light extinction turret 20 is a member forming the disk shape configured by a plurality of types of light extinction mesh filters with different light extinction rates arranged on the coaxial circumferences. At the center of the disk face of this light extinction turret 20, the motor 23 is connected. This motor 23 is to rotate the light extinction turret 20 on the basis of the control signal inputted from the control portion 15 so that any one of the light extinction mesh filters is located on the light path of the illumination light having passed the diaphragm 19. The light extinction mesh filter is used here as the light extinction filter, but it is not limited thereto.

The above-mentioned plural types of light extinction mesh filters have respective light extinction rates corresponding to the type of the endoscope 2 to be connected to the light source device 4, that is, the respective light extinction rates corresponding to the maximum light amount which can enter a light guide fiber of the endoscope 2. The control portion 15 outputs a control signal to the motor 23 so that the light extinction mesh filter corresponding to the connected endoscope 2 is located on the light path of the illumination light on the basis of the endoscope detection signal outputted from the above-mentioned endoscope detection portion 25. Therefore, even if the diaphragm 19 is fully opened, not all the light amount of the illumination light generated at the main lamp 17 enters the endoscope 2. That is, the illumination light generated at the main lamp 17 is reduced by the light extinction turret 20, and the illumination light with the maximum light amount which can enter the connected endoscope 2 as the upper limit enters the endoscope 2.

The illumination light having entered the light guide fiber of the endoscope 2 in this way illuminates a subject through the lens 12 from the tip end portion of the insertion portion of the endoscope 2. The reflected light from the illuminated subject is captured by the CCD 13 arranged at the tip end portion of the insertion portion of the endoscope 2. The image pickup signal from this CCD 13 is inputted to the video processor 3 through the connector 10 connecting the endoscope 2 to the video processor 3.

The video processor 3 has an image processing circuit, not shown, and executes various image processing and outputs an image signal after the processing to the monitor 5. Also, the video processor 3 extracts a brightness signal as information on brightness of the image from the image signal and outputs this brightness signal to the control portion 15 through the connector 11 of the light source device 4.

If the manual light control mode is set here, the control portion 15 outputs a control signal of the motor 22 to operate the diaphragm 19 to the motor 22 to have the light amount operated/inputted from the front panel 26 and set irrespective of the inputted brightness signal.

On the other hand, if the automatic light control mode is set, the control portion 15 controls the light amount so that the brightness signal inputted from the video processor 3 becomes the brightness operated/inputted and set from the front panel 26. That is, the control portion 15 outputs a control signal of the motor 22 to operate the diaphragm 19 so as to obtain the set brightness to the motor 22. Specifically, the control portion 15 outputs a control signal to operate the diaphragm 19 to be opened when the brightness indicated by the brightness signal is lower than the set brightness, while it outputs a control signal to operate the diaphragm 19 to be closed when the brightness indicated by the brightness signal is higher than the set brightness.

As mentioned above, this endoscope system 1 enables observation of the subject by emitting the illumination light generated at the light source device 4 to the subject. Also, this endoscope system 1 can automatically control the illumination light amount on the basis of the brightness of an observed image when set to the automatic light control mode. Moreover, the endoscope system 1 enables the operator to control the illumination light to a desired light amount by operation through the front panel 26 when set to the manual light control mode.

The configuration of light-amount control processing to have the light amount with a predetermined value when the endoscope 2 and the video processor 3 are not connected in the automatic light control mode or when the video processor 3 and the light source device 4 are not connected, which is a characteristic of the present embodiment, will be described below. The non-connection in the present embodiment (or "not connected") is a state where signal communication between the devices is not carried out normally such as a case where nothing is connected, connection is not complete, power is turned off, connection is disconnected, disconnection occurs in a cable or a connector or the like.

The control portion 15 as the first connection detecting means detects the connection state between the endoscope 2 and the video processor 3 at the connector 10. In the present embodiment, the control portion 15 detects the connection state based on whether a predetermined signal is inputted to the control portion 15 from the video processor 3 or not. This predetermined signal is to be a first connection signal. The connection state at this connector 10 is monitored all the time as long as the power of the light source device 4 is on.

Similarly, the control portion 15 as the connection detecting means and the second connection detecting means detects the connection state between the video processor 3 and the light source device 4 at the connector 11. In the present embodiment, the control portion 15 detects the connection state based on whether a predetermined signal is inputted to the control portion 15 from the video processor 3 or not. This predetermined signal is to be a second connection signal. The connection state at the connector 11 is monitored all the time as long as the power of the light source device 4 is on. The above-mentioned first and second connection signals will be described later.

Also, the control portion 15 detects the connection state of the video processor 3 on the basis of availability of input of the second connection signal, but the connection state may be detected using another means. For example, the control portion 15 may receive information on power voltage of the video processor 3 inputted from the video processor 3 and make determination so as to detect whether the video processor 3 is connected or not.

And if at least one of the connector 10 and the connector 11 is not connected in the automatic light control mode, that is, if the bright signal is not inputted from the video processor 3, the control portion 15 operates the diaphragm 19 and controls the light amount of the illumination light to a predetermined light amount. Specifically, the control portion 15 outputs a control signal to the motor 22 and fixes an opening degree value of the diaphragm 19 to a predetermined value.

The above-mentioned predetermined light amount means the minimum illumination light amount enabling observation of the subject. This predetermined light amount is, in the present embodiment, achieved by controlling the diaphragm 19 to an opening degree value almost at the half of the maximum value of the opening degree value (hereinafter, referred to as a diaphragm half open value). Also, in the present embodiment, the brightness achieved by the light amount of this diaphragm half open value is the brightness substantially equal to that of the spare lamp 24.

As mentioned above, the plurality of types of endoscopes 2 which can be used for the endoscope system 1 have different maximum incident light amounts, and the plurality of types of light extinction mesh filters provided at the light extinction turret 20 have different light extinction rates according to the connected endoscope 2. Therefore, the diaphragm half open value is set considering the light extinction rate of the light extinction mesh filter corresponding to the respective endoscopes 2. And the control portion 15 stores the plurality of diaphragm half open values according to the type of the endoscope 2 in advance.

In the manual light control mode, since the light amount is controlled manually, control by the control portion 15 is not affected even if at least one of the connector 10 and the connector 11 is not connected.

In this way, the endoscope system 1 can have the light amount at the predetermined value when the endoscope 2 and the video processor 3 are not connected or when the video processor 3 and the light source device 4 are not connected in the automatic light control mode.

Moreover, the configuration on the above-mentioned light amount control will be described in detail referring to FIGS. 2 and 3.

Figure 2:
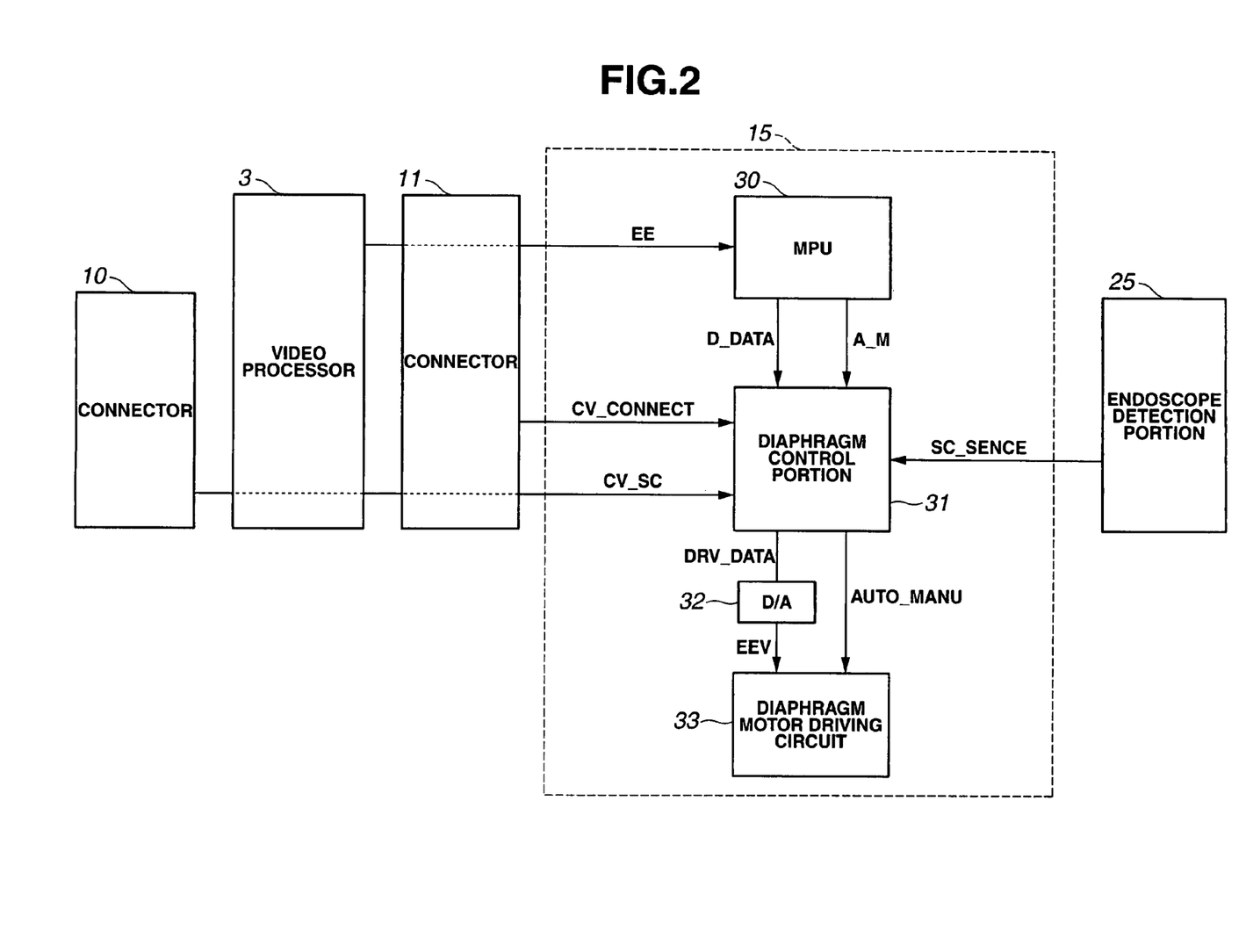
FIG. 2 is a block diagram showing an outline configuration relating to light amount control along with an example of a signal flow in the embodiment.

FIG. 2 is a block diagram showing a configuration relating to the light amount control along with an example of a flow of a signal. As shown in FIG. 2, the control portion 15 comprises a microprocessor unit (hereinafter and in figures, abbreviated as MPU) 30, a diaphragm control portion 31, a digital/analog conversion circuit (hereinafter and in figures, abbreviated as D/A) 32 and a diaphragm motor driving circuit 33.

As mentioned above, to the control portion 15, an endoscope detection signal SC_SENCE is inputted from the endoscope detection portion 25 and a brightness signal EE is inputted from the video processor 3 through the connector 11. Also, when the endoscope 2 and the video processor 3 are connected, a first connection signal CV_SC is inputted to the control portion 15 from the video processor 3. Similarly, when the video processor 3 and the light source device 4 are connected, a second connection signal CV_CONNECT is inputted to the control portion 15 from the video processor 3.

The brightness signal EE having a value corresponding to the brightness of a captured image among the above-mentioned various signals is inputted to the MPU 30 of the control portion 15. Then, when the light source device 4 is set to the automatic light control mode, the MPU 30 generates an opening degree value signal D_DATA representing an opening degree value of the diaphragm 19 on the basis of this brightness signal EE and the brightness as a target set at the front panel 26. On the other hand, when the light source device 4 is set to the manual light control mode, the MPU 30 generates an opening degree value signal D_DATA representing an opening degree value of the diaphragm 19 for generating the light amount set at the front panel 26. Then, the MPU 30 outputs the opening degree value signal D_DATA to the diaphragm control portion 31.

Also, substantially at the same time, the MPU 30 outputs a light control mode signal A_M representing whether the currently set light control mode is the manual light control mode or the automatic light control mode to the diaphragm control portion 31. This light control mode signal A_M is a binary signal having a high ("1", for example) value when the set light control mode is the automatic light control mode and a low ("0", for example) value when it is the manual light control mode.

To the diaphragm control portion 31, the above-mentioned opening degree value signal D_DATA and the light control mode signal A_M are inputted and moreover, the first connection signal CV_SC, the second connection signal CV_CONNECT and the endoscope detection signal SC_SENCE are inputted.

The endoscope detection signal SC_SENCE among these signals is a signal having a value specific to the connected endoscope 2, that is, a signal which can identify the type of the connected endoscope 2.

Also, the first connection signal CV_SC is inputted to the diaphragm control portion 31 when the endoscope 2 and the video processor 3 are connected. At this time, the first connection signal CV_SC has a high ("1", for example) value. On the other hand, when the endoscope 2 and the video processor 3 are not connected, the first connection signal CV_SC is not inputted to the diaphragm control portion 31. At this time, the first connection signal CV_SC has a low ("0", for example) value.

Moreover, the second connection signal CV_CONNECT is inputted to the diaphragm control portion 31 when the video processor 3 and the light source device 4 are connected. At this time the second connection signal CV_CONNECT has a high ("1", for example) value. On the other hand, when the video processor 3 and the light source device 4 are not connected, the second connection signal CV_CONNECT is not inputted to the diaphragm control portion 31. At this time, similar to the above, the second connection signal CV_CONNECT has a low ("0", for example) value.

The diaphragm control portion 31 determines and outputs a diaphragm motor driving signal DRV_DATA and a light control circuit selection signal AUTO_MANU according to each of the above-mentioned input signals. The diaphragm motor driving signal DRV_DATA among them is a driving signal for driving the motor 22 for operating the diaphragm 19. Also, the light control circuit selection signal AUTO_MANU is a signal for selecting either one of a manual light control circuit and an automatic light control circuit provided at the diaphragm motor driving circuit 33. The manual light control circuit is used when the opening degree value of the diaphragm 19 is fixed to a specific value. On the other hand, the automatic light control circuit is used when the opening degree value of the diaphragm 19 is controlled by the MPU 30. And the light control circuit selection signal AUTO_MANU is a binary signal having a high ("1", for example) value when the automatic light control circuit is used and a low ("0", for example) value when the manual light control circuit is used.

Figure 3:
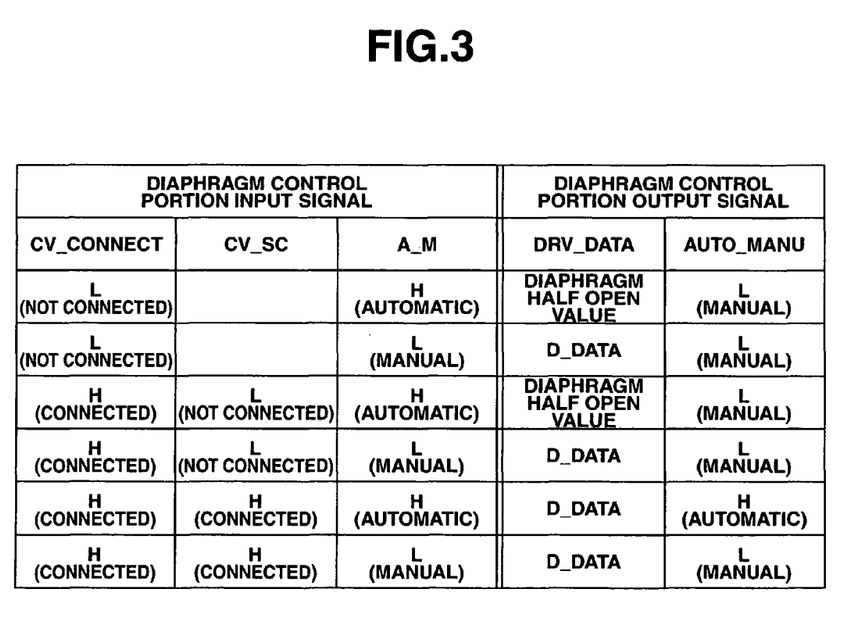
FIG. 3 is a table showing a relation between an input signal and an output signal in a diaphragm control portion of the embodiment.

How the diaphragm control portion 31 determines the diaphragm motor driving signal DRV_DATA and a light control circuit selection signal AUTO_MANU according to each of the inputted signals is shown in FIG. 3. FIG. 3 is a table showing a relation between the input signal and the output signal at the diaphragm control portion 31.

As shown in the figure, when the second connection signal CV_CONNECT is low, that is, when the video processor 3 and the light source device 4 are not connected, the first connection signal CV_SC from the video processor 3 is not naturally inputted to the control portion 15 of the light source device 4.

And at this time, there are two cases of a case where the light control mode signal A_M is high, that is, the light source device 4 is set to the automatic light control mode and a case where the light control mode signal A_M is low, that is, the light source device 4 is set to the manual light control mode.

First, if the light control mode signal A_M is high and the light source device 4 is set to the automatic light control mode, the diaphragm motor driving signal DRV_DATA outputted from the diaphragm control portion 31 becomes a diaphragm half open value. And the diaphragm control portion 31 sets the light control circuit selection signal AUTO_MANU at low in order to obtain the opening degree value of the diaphragm 19 at a predetermined value and controls so that the manual light control circuit is used.

On the other hand, if the light control mode signal A_M is low and the light source device 4 is set to the manual light control mode, the diaphragm motor driving signal DRV_DATA outputted from the diaphragm control portion 31 becomes the opening degree value signal D_DATA corresponding to the target light amount set by the front panel 26. Also, since the light source device 4 is in the manual light control mode, the diaphragm control portion 31 controls by setting the light control circuit selection signal AUTO_MANU at low so that the manual light control circuit is used.

Next, when the second connection signal CV_CONNECT is high, that is, the video processor 3 and the light source device 4 are connected, there are two cases of a case where the first connection signal CV_SC is high, that is, when the endoscope 2 and the video processor 3 are connected and a case where the first connection signal CV_SC is low, that is, when the endoscope 2 and the video processor 3 are not connected.

First, when the first connection signal CV_SC is low and the endoscope 2 and the video processor 3 are not connected, if the light control mode signal A_M is high, that is, in the automatic light control mode, the diaphragm motor driving signal DRV_DATA becomes a diaphragm half open value. On the other hand, if the light control mode signal A_M is low, that is, in the manual light control mode, the diaphragm motor driving signal DRV_DATA becomes the opening degree value signal D_DATA corresponding to the target light amount set by the front panel 26. And in either cases, the light control circuit selection signal AUTO_MANU is low in order to have the opening degree value of the diaphragm 19 at the predetermined value.

On the other hand, when the first connection signal CV_SC is high and the endoscope 2 and the video processor 3 are connected, that is, when all are connected, if the light control mode signal A_M is high, that is, in the automatic light control mode, the diaphragm motor driving signal DRV_DATA becomes the opening degree value signal D_DATA determined on the basis of the target brightness set by the front panel 26 and the brightness signal EE, and the control of the diaphragm 19 also becomes automatic. Therefore, the light control circuit selection signal AUTO_MANU is high.

On the contrary, when the light control mode signal A_M is low, that is, in the manual light control mode, the diaphragm motor driving signal DRV_DATA becomes the opening degree value signal D_DATA corresponding to the target light amount set by the front panel 26. Also, the light control circuit selection signal AUTO_MANU is low in order to have the opening degree value of the diaphragm 19 at a predetermined value.

In this way, the diaphragm control portion 31 determines and outputs the diaphragm motor driving signal DRV_DATA and the light control circuit selection signal AUTO_MANU. The light control circuit selection signal AUTO_MANU in these two types of output signals is outputted as it is to the diaphragm motor driving circuit 33 from the diaphragm control portion 31.

Also, the diaphragm motor driving signal DRV_DATA outputted from the diaphragm control portion 31 is inputted to the D/A 32, converted from a digital signal to an analog signal to become an analog driving signal EEV. The analog driving signal EEV is inputted to the diaphragm motor driving circuit 33.

The diaphragm motor driving circuit 33 has, as mentioned above, a driving circuit for automatic light control and a driving circuit for manual light control, and one of the driving circuits is selected according to the inputted light control circuit selection signal AUTO_MANU. And the selected driving circuit is driven by the inputted analog driving signal EEV and controls the opening degree value of the diaphragm 19 by operating the motor 22.

As mentioned above, when non-connection occurs between the endoscope 2 and the video processor 3 or between the video processor 3 and the light source device 4 due to defective connection, for example, since it is so configured that the light source device 4 emits a predetermined light amount for the illumination light amount according to the type of the connected endoscope 2, excessively small or excessively large illumination light is not supplied to the endoscope. By this, the minimum light amount required for observation can be ensured, and halation of an image and heat generation caused by irradiation of excessive illumination light can be prevented.

In the present embodiment, a plurality of filters are provided at the turret 18, but the light amount might be reduced when the illumination light passes through any of these filters. Therefore, it may be so configured that a light extinction mesh filter of the light extinction turret 20 can be selected according to the filter on the turret 18 through which the illumination light passes.

Also, in the present embodiment, as means for controlling the light amount to a predetermined one, means for controlling the opening degree value of the diaphragm 19 is used, but not limited to this, means for controlling electric power to be supplied to the main lamp 17, for example, (this is made possible by controlling the switching regulator 16) may be used or means for controlling the light extinction filter located on the light path of the illumination light by rotating the light extinction turret 20 (this is made possible by controlling the motor 23) may be used. Moreover, two or more of these means may be combined.

Moreover, in the present embodiment, the connection state at the connector 10 and the connector 11 is detected by the control portion 15 by the value of the first connection signal CV_SC and the value of the second connection signal CV_CONNECT inputted through the connector 11 to which the video processor 3 is connected, respectively. However, not limited to this, it may be so configured that the connection state between the endoscope 2 and the video processor 3 is detected by the connector 10, the first connection signal CV_SC representing the detection result is outputted to the control portion 15, the connection state between the video processor 3 and the light source device 4 is detected by the connector 11, and the second connection signal CV_CONNECT representing the detection result is outputted to the control portion 15.

Figure 4:
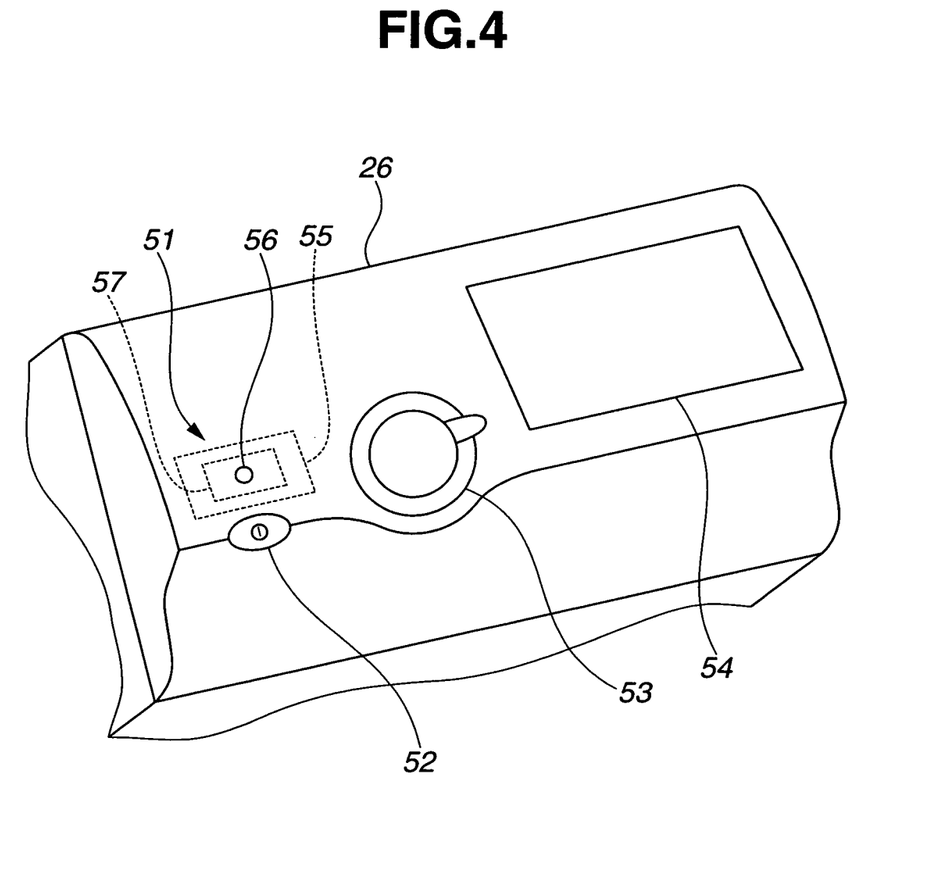
FIG. 4 is a view showing an outline appearance of a front panel in the embodiment.

The light source device 4 in the present embodiment has a light emitting diode (hereinafter referred to as LED) indicating the light source device 4 is turned on at the front panel 26.

The configuration of the front panel 26 will be described below referring to the attached drawings.

FIG. 4 is a view showing an outline appearance of the front panel 26. On this front panel 26, an LED portion 51, a power switch 52, an endoscope connection portion 53 and an operation switch portion 54 are arranged.

The LED portion 51 has an LED substrate 55 disposed on the inner face side of the front panel 26, an LED 56 mounted on this LED substrate 55 and an LED cover 57 for covering the LED 56.

Also, the power switch 52 is a switch configured so that the power of the light source device 4 is turned on when pressed. When the power switch 52 is pressed and the power of the light source device 4 is turned on, the above-mentioned LED 56 is lighted.

Moreover, the endoscope connection portion 53 is a connection terminal portion for connecting the endoscope 2.

And the operation switch portion 54 has various switches arranged for operating this light source device 4.

Next, the LED portion 51 will be described. First, FIG. 5 is a perspective view showing an outline appearance of the LED substrate 55.

Figure 5:
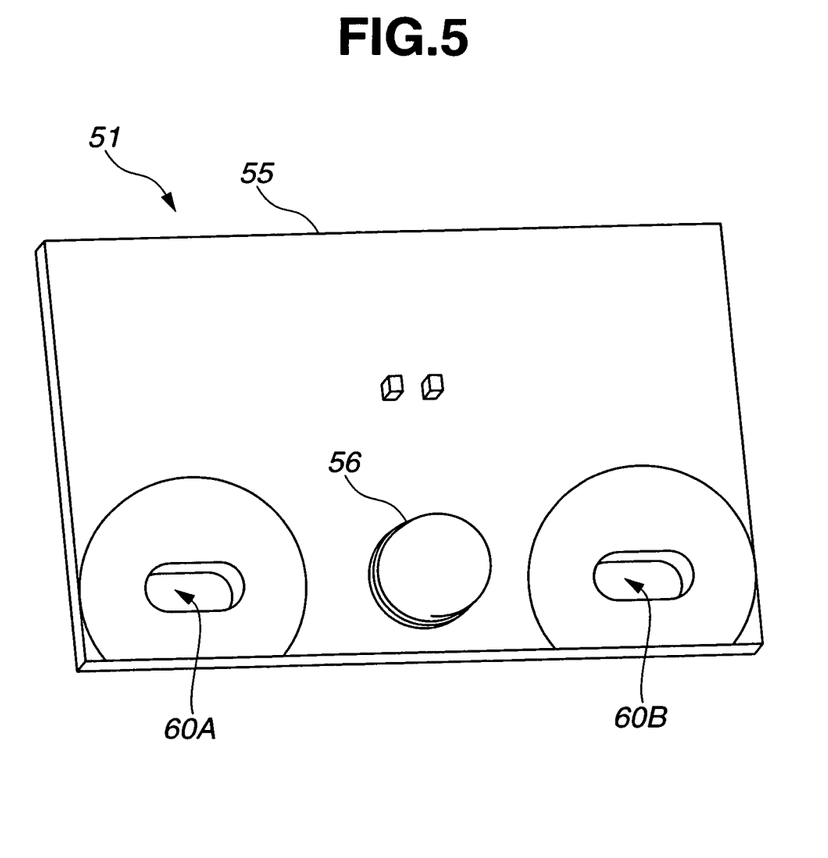
FIG. 5 is a perspective view showing an outline appearance of an LED substrate in the embodiment.

As shown in FIG. 5, the LED 56 is mounted on the LED substrate 55. Also, on the LED substrate 55, a hole 60A and a hole 60B for mounting the LED substrate 55 to this front panel 26 are provided. These holes 60A, 60B are formed as laterally long holes as in the figure.

Figure 6:
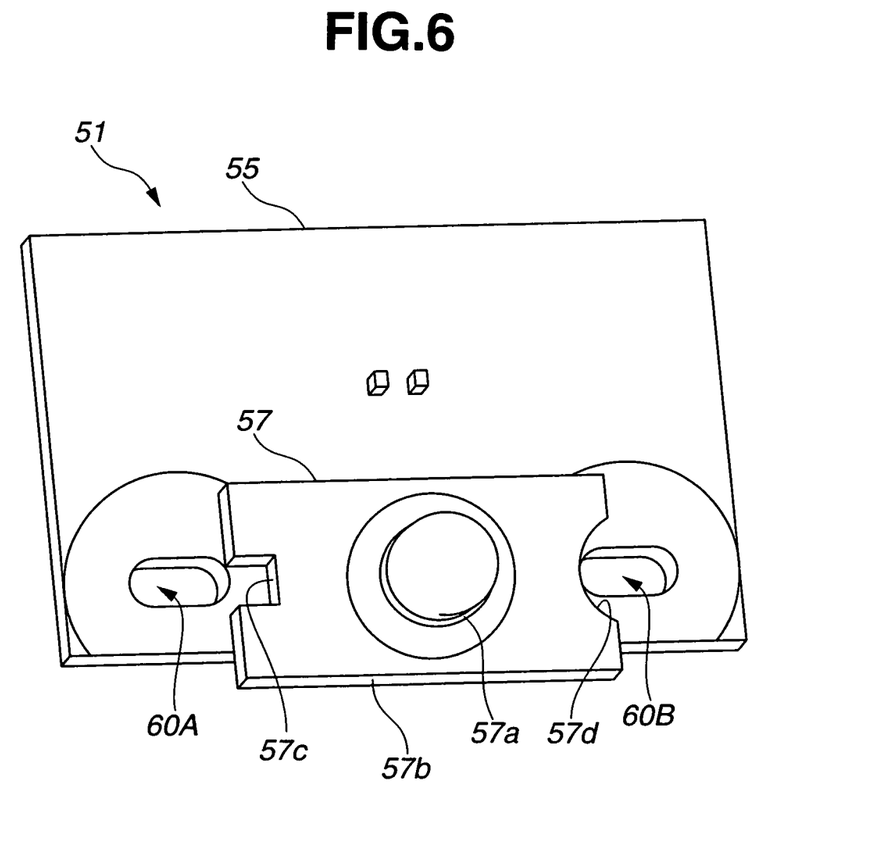
FIG. 6 is a perspective view showing an outline appearance of the LED substrate when an LED cover is attached in the embodiment.

Next, FIG. 6 is a perspective view showing an outline appearance of the LED substrate 55 when the LED cover 57 is attached.

As shown in FIG. 6, the LED cover 57 is arranged so as to cover the whole LED 56. The LED cover 57 is formed by a material having light transmission to have a head portion 57a, which is a portion covering the LED 56, and a leg portion 57b, which is a portion other than this head portion 57a. And this LED cover 57 is formed in the shape so that the hole 60A and the hole 60B of the LED substrate 55 are not blocked. Specifically, a notch 57c in the rectangular shape is formed on the hole 60A side of the LED cover 57 and an arc-state notch 57d on the hole 60B side of the LED cover 57, respectively. Also, the LED cover 57 is formed by a non-conductive resin, for example, so as to prevent mixture of electric external noise.

Figure 7:
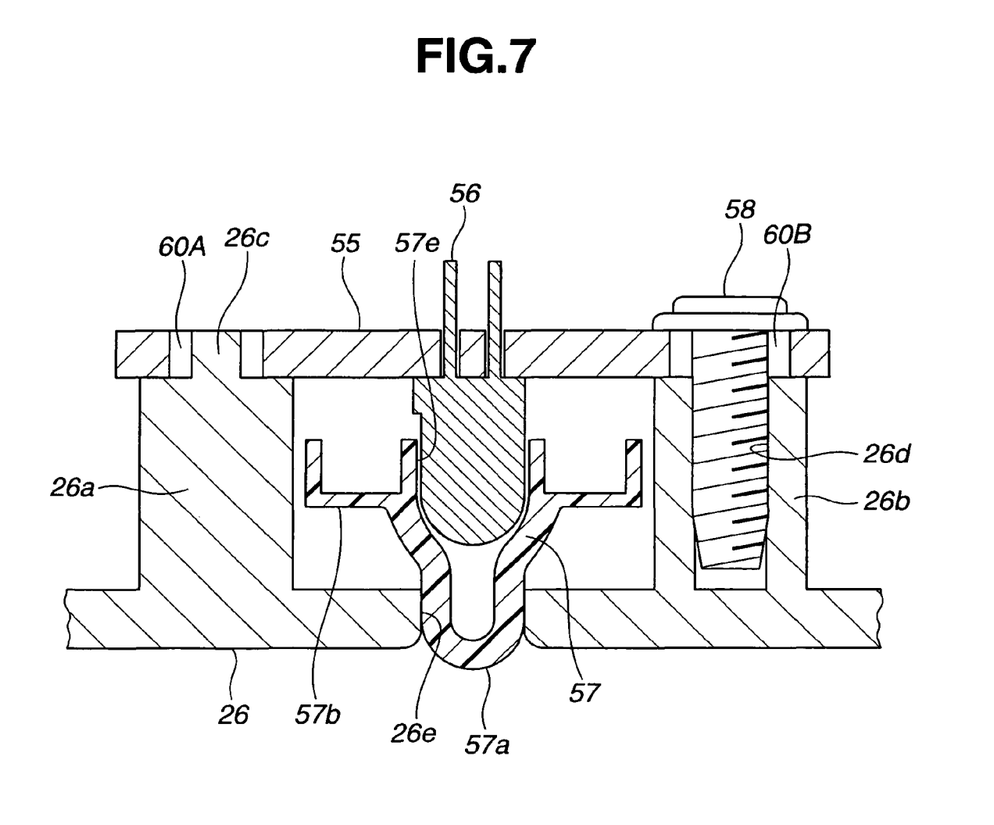
FIG. 7 is a sectional view showing an outline configuration of an LED portion on the front panel to which the LED substrate is mounted in the embodiment.

Then, FIG. 7 is a sectional view showing an outline configuration of the LED portion 51 in the front panel 26 on which the LED substrate 55 is mounted.

As shown in FIG. 7, two columnar projections 26a, 26b are formed on the inner face side of the front panel 26. At the tip end portion of the projection 26a of these projections, a smaller projection 26c is formed to be fitted in the hole 60A of the LED substrate 55. Also, on the other projection 26b, a screw hole 26d is formed in the columnar shape inside, and by screwing a small screw 58 through the hole 60B of the LED substrate 55, the LED substrate 55 is connected to the front panel 26.

The LED 56 mounted to the LED substrate 55 fixed in this way is located between the front panel 26 and the LED substrate 55. Also, at a position opposite to the LED 56 of the front panel 26, a hole 26e is provided for allowing passage of light emitted from the LED 56 to the outer face side of the front panel 26. The hole 26e is formed at the location, with the size and shape so that the head portion 57a of the LED cover 57 is fitted in.

The head portion 57a of the LED cover 57 is formed with a section in the shell state in the substantial semisphere, and the inner diameter of the shell-state semisphere portion is smaller than the outer diameter of the LED 56. Therefore, when the LED cover 57 is mounted so as to cover the LED 56, an internal space is formed between the head portion 57a and the LED 56.

Also, a fitting portion 57e at the leg portion 57b of the LED cover 57 is fitted on the outer circumferential face of the LED 56.

This LED cover 57 has such a structure that the light from the LED 56 can be visually checked even from a wide range of observation angle (that is, a wide view angle) when the LED 56 is observed at various angles from the outer face side of the front panel 26.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A light source device to which an endoscope and an image processing device can be connected, comprising:
   a light source of illumination light;
   connection detecting means for detecting whether the image processing device is connected or not;
   endoscope detecting means for detecting the type of the connected endoscope; and
   illumination light control means for controlling so that a light amount of the illumination light has a predetermined light amount based on the type of the endoscope detected by the endoscope detecting means when it is detected that the image processing device is not connected by the connection detecting means.

2. The light source device according to claim 1, wherein the connection detecting means detects whether the image processing device is connected or not on the basis of information on power voltage of the image processing device inputted from the image processing device.

3. The light source device according to claim 1, wherein the illumination light control means has a diaphragm arranged on the light path of the illumination light and controls so that the light amount of the illumination light becomes the predetermined light amount by controlling an opening degree value of the diaphragm.

4. The light source device according to claim 1, wherein the illumination light control means has a plurality of types of light extinction filters with different light extinction rates and controls so that the light amount of the illumination light becomes the predetermined light amount by controlling the light extinction filter arranged on the optical path of the illumination light.

5. The light source device according to claim 1, wherein the illumination light control means has power supply control means for controlling power to be supplied to the light source and controls so that the light amount of the illumination light becomes the predetermined light amount by controlling the power to be supplied to the light source by the power supply control means.

6. The light source device according to claim 1, wherein the illumination light control means controls so that the light amount of the illumination light becomes the predetermined light amount when it is detected by the connection detecting means that the image processing device is not connected in an automatic light control mode for automatically controlling the light amount of the illumination light on the basis of brightness of an observed image.

7. The light source device according to claim 1, further comprising a spare light source with a light amount smaller than that of the light source and wherein the predetermined light amount is substantially the same as the light amount of the spare light source.

8. An endoscope system comprising an image processing device and a light source device and to which the endoscope can be connected, further comprising:
- first connection detecting means for detecting whether the endoscope and the image processing device are connected or not;
- second connection detecting means for detecting whether the image processing device and the light source device are connected or not;
- endoscope detecting means for detecting the type of the endoscope connected to the light source device; and
- illumination light control means for controlling so that the light amount of the illumination light supplied from the light source device to the endoscope becomes a predetermined light amount according to the type of the endoscope detected by the endoscope detecting means when it is detected by the first connection detecting means that the endoscope and the image processing device are not connected or when it is detected by the second connection detecting means that the image processing device and the light source device are not connected.

* * * * *